United States Patent [19]

Rey et al.

[11] Patent Number: 4,497,074
[45] Date of Patent: Feb. 5, 1985

[54] ORGAN PROSTHESES

[75] Inventors: Pierre Rey, Thorigny; Jacqueline Leandri, Paris; Clément Abbou, Fontenay-sous-Bois, all of France

[73] Assignee: Agence National de Valorisation de la Recherche (ANVAR), Seine, France

[21] Appl. No.: 43,677

[22] Filed: May 30, 1979

Related U.S. Application Data

[62] Division of Ser. No. 784,377, Apr. 4, 1977, abandoned.

[30] Foreign Application Priority Data

Apr. 5, 1976 [FR] France ................................ 76 09794
Mar. 10, 1977 [FR] France ................................ 77 07091

[51] Int. Cl.³ ............................ A61F 1/00; A61F 1/24
[52] U.S. Cl. .................................................. 3/1; 3/1.4; 3/1.7; 264/221; 264/304; 264/317
[58] Field of Search ................ 264/221, 304; 3/1, 1.5, 3/1.417, 1 A

[56] References Cited

U.S. PATENT DOCUMENTS

| | | | |
|---|---|---|---|
| 1,876,229 | 9/1932 | Herzog | 264/304 |
| 2,186,468 | 1/1940 | Schwartz | 264/221 |
| 2,550,206 | 4/1951 | Teston | 264/304 |
| 3,453,194 | 7/1969 | Bennett et al. | 3/1 |
| 3,512,183 | 5/1970 | Sharp et al. | 3/1 |
| 3,708,324 | 1/1973 | Stebleton | 3/1 |
| 3,978,187 | 8/1976 | Fletcher | 264/304 |
| 4,311,659 | 1/1982 | Rey | 264/304 |

FOREIGN PATENT DOCUMENTS

| | | | |
|---|---|---|---|
| 103435 | 3/1938 | Australia | 264/304 |
| 7340939 | 6/1975 | France . | |
| 7412107 | 10/1975 | France . | |

Primary Examiner—James Derrington
Attorney, Agent, or Firm—Antonelli, Terry & Wands

[57] ABSTRACT

Organ prostheses are manufactured starting from a support preformed in the shape of the prosthesis to be formed on which a sol giving on cooling a gel enabling a surface state approximating to that of a liquid-air interface is deposited, a hardenable flexible material compatible with body tissues is deposited thereon and the prosthesis removed from the mould. Ureter, bladder, vascular and cardiac prostheses made by this method are disclosed.

44 Claims, 10 Drawing Figures

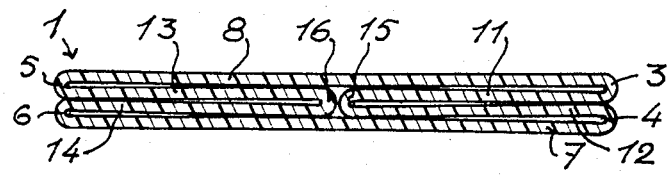
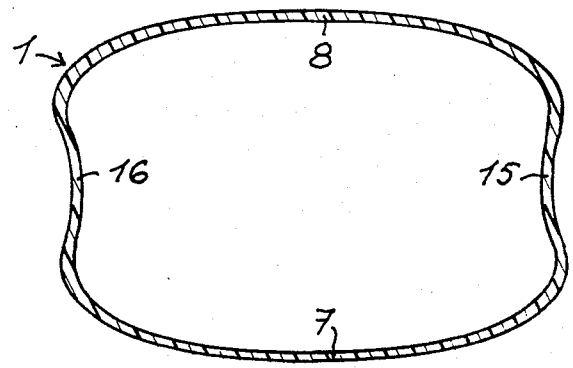
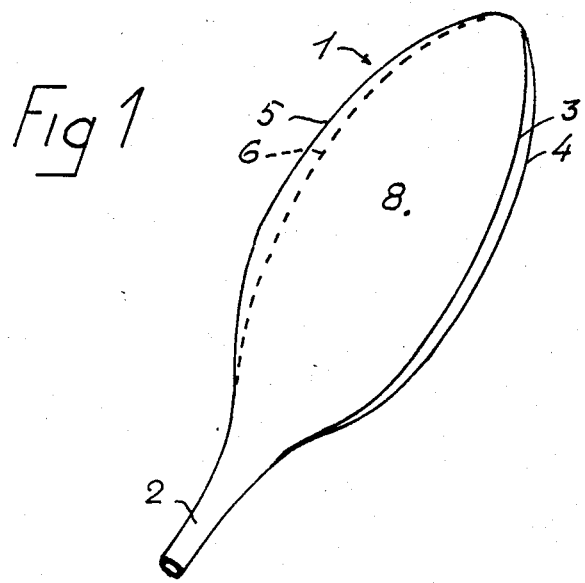

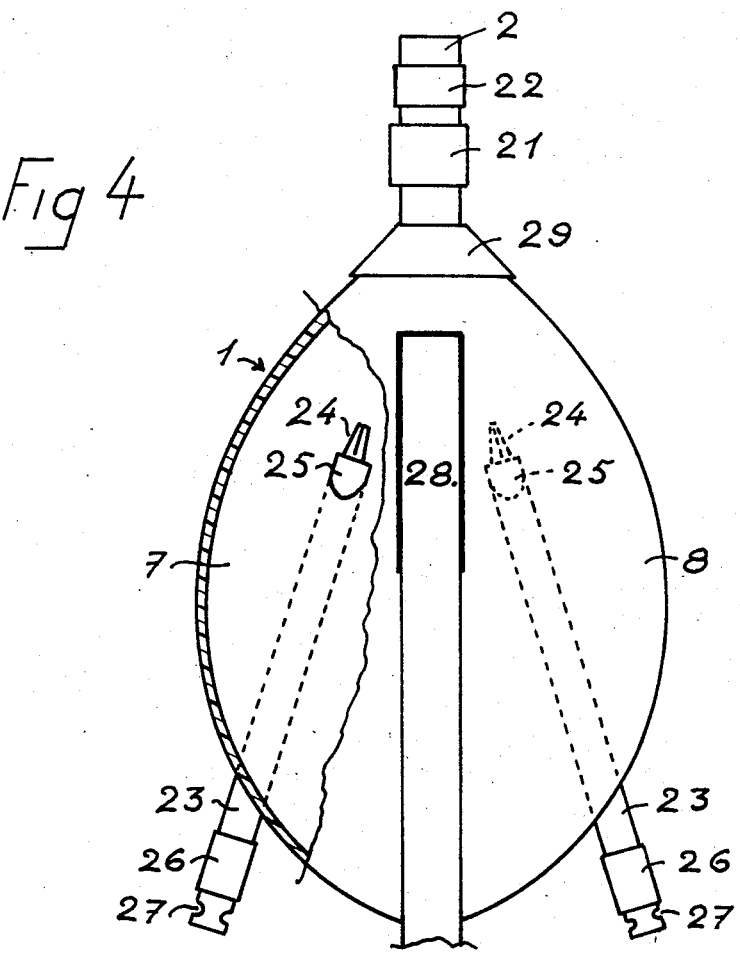
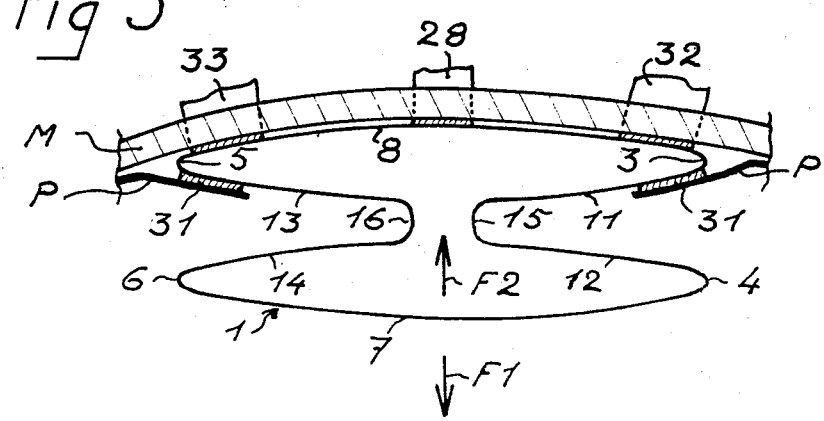

ORGAN PROSTHESES

This is a division of application Ser. No. 784,377, filed Apr. 4, 1977, now abandoned.

FIELD OF THE INVENTION

The present invention relates to a process for the manufacture of organ prostheses and to organ prostheses obtained by this process.

In certain cases, it is of prime importance that the inner faces of organ prostheses should have a perfect surface state; in fact, the slightest surface imperfection or irregularity is in the more or less short term the source of the formation of concretions or deposits which are liable to lead to blocking of the organ or to serious organic injuries, the outcome of which may be fatal for a patient wearing such a prosthesis.

DESCRIPTION OF THE PRIOR ART

A certain number of attempts to obtain perfect non-adherent states of prosthetic surfaces have been made by research workers and thus it is that it has been proposed to coat prosthetic surfaces in contact with living tissues or with biological liquids with various substances capable of giving the objects that they cover a sufficiently perfect surface state to prevent the formation of concretions and deposits. Among the coatings proposed according to the prior art, can be mentioned coatings constituted by a silicone, or coatings constituted by a liquid organo-silicon composition hardenable to constant volume, generally in the presence of a catalyst such as a tin derivative, which is toxic, or of a peroxide or a platinum derivative. It is, however, possible to apply these coatings to the surfaces to be treated only after preparation of the latter by applying a "primary" adhesion layer (except if these surfaces are themselves of silicone). The solutions proposed according to the prior art have the disadvantage of requiring relatively complex coating operations.

Consequently, an object of the present invention is to provide a process for the manufacture of organs which meets practical requirements better than previously known processes having the same aim, and in particular which enables artificial organs to be obtained which present an internal surface state which is substantially perfect and totally devoid of roughness which could be the source of the formation of concretions and deposits, and avoid risks of accidental circulatory complications (due to the formation of fibrinous coagulum), lithiasis or formation of calculi, which are incurred by patients wearing prostheses known in the prior art. Moreover, the process according to the present invention enables prostheses to be obtained with shapes which it has not been possible to obtain by the conventional moulding processes, all of which utilize rigid moulds which can be dismantled. Finally, the process to which the present invention relates enables prostheses which are satisfactory from the medical point of view to be obtained.

SUMMARY OF THE INVENTION

According to the present invention, there is provided a process for the manufacture of organ prostheses which is characterised in that a start is made from a support preformed in the shape of the prosthesis to be obtained, on which, in the course of a first stage, a sol giving, on cooling, a gel enabling a surface state close to that of the liquid-air interface to be obtained at the gel-air interface is deposited by dipping, spraying, coating, varnishing, lacquering, etc., after which, in the course of a second stage, a hardenable flexible material, such as preferably a silicone elastomer, or any other hardenable flexible material compatible with the body liquids and tissues is deposited by dipping, flowing, spraying, etc. on the "mould" obtained in this way, and then, in the course of a third stage after hardening of the said material, the prosthesis obtained is removed from the mould by any suitable means.

According to an advantageous embodiment of the process of the invention, the preformed support used for carrying out the moulding of prostheses is a support preformed from non-eliminable material, such as metal, glass, plastics material, etc. which has an appropriate surface state without any rough or uneven areas, on which is deposited a sol which gives, on cooling, a gel on which is deposited a hardenable flexible material, after hardening of which the gel is eliminated by reheating, washing and dissolution, after which the support, whose dimensions are smaller than those of the moulded prosthesis in consequence of the elimination of the gel, is withdrawn from the moulded prosthesis by a simple sliding action.

According to another advantageous embodiment of the process of the invention, the preformed support used for carrying out the moulding of prostheses is obtained by moulding a core of completely eliminable material, such as wax, ceresin or a sol giving a gel on cooling, in a removable or dismantlable mould of material such as metal, plastics material, etc., the surfaces of which are devoid of any unevenness, and then, after releasing the core obtained in this way from the mould by removal of the latter, treating the surface of this support core with a sol capable of giving a gel by cooling, after which a hardenable flexible material such as silicone elastomer, for example, is deposited on the support core obtained in this way and then, after hardening of the said flexible material, the support core is eliminated by melting and then dissolution with a hot liquid.

According to an advantageous embodiment of the process of the invention, the sol by cooling of which there is formed a gel adapted to give a surface state close to that of the liquid-air interface at the gel-air interface is preferably gelose or gelatin in solution.

In the case where the support core is composed of an eliminable material constituted by a sol capable of giving a gel by cooling, this material is preferably gelose or gelatin in solution.

According to a modified form of the process of the invention, when the support core of eliminable material is constituted by a gel formed from a sol constituted by gelose in solution, it is not necessary to carry out a supplementary application, to such a core, of sol giving rise to a gel and, in order to obtain a surface state close to that of the liquid-air interface at the gel-air interface, it is sufficient to subject the said gel to the action of heat prior to deposit of the hardenable flexible material intended to form the prosthesis.

The present invention also provides organ prostheses produced by carrying into effect the process of the invention as defined above.

In particular, the present invention provides an implantable artificial bladder associated or not with complete ureters, and/or with artificial urethras, and to simple or complex vascular prostheses with collateral branches or bifurcations, valvular prostheses, in particular valvular elements of the type according to French Patent No. 74 12107, cardiac prostheses and more particularly ventricular and/or auricular cavities, and prostheses of very small calibre designed to be used in microsurgery, in particular in neurological microsurgery for example, for replacing brain vessels, in cardiac microsurgery, for example, for replacing coronary vessels, and in digestive microsurgery, for example, for replacing the choledoch canal, the splenic, mesenteric, etc. vessels, microvessels and microcanals, which it has been impossible to obtain heretofore with a perfect internal surface state.

As regards implantable artificial bladders, the need for such a prosthesis has been apparent for a long time in medicine and surgery, and also in biological research.

In the present state of the known art, there are already implantable artificial bladders in existence. These bladders, however, have major and even latent disadvantages: some of these bladders cannot be emptied completely and the residual volume of urine entails exposure to a great degree to the risk of the appearance of lithiasis or calculi or other concretions, the material of which some of these bladders are made and the surface state of this material entail exposure to a great degree to the same risk, some of these bladders do not comprise valves for the ureters and the urine may flow back towards the renal calyxes, and some of these bladders cannot accept a urethral sphincter.

Consequently, the present invention also has the object of providing an implantable artificial bladder which meets practical requirements better than the implantable artificial bladders heretofore known, in particular in that it can be emptied completely, in that its material and the surface state of this material do not cause the appearance either of lithiasis, or of calculi or other concretions, in that its ureters are provided with valves prohibiting the flowing back of urine, in that it can be provided with a urethral sphincter and in that it has a shape which lends itself particularly well to its implantation in the minor pelvis and to its suspension and attachment.

The present invention relates to an implantable artificial bladder of flexible material and of ovoid general shape, characterised in that, in the empty state or in the absence of internal pressure, it has in transverse cross-section the form of two W's lying in opposite directions and jointed together symmetrically by their outer legs and in which the inner apices substantially touch and the four legs of each W are in contact substantially everywhere in pairs, in that its surfaces in contact with urine are in a perfect surface state, and in that it is provided with means of suspension at at least three points.

According to a preferred embodiment of the bladder to which the present invention relates, it is extended at one end of its ovoid general shape by a urethral tube which can be provided with an artificial sphincter of a type per se for example of the type according to French Patent No. 73 40939 and with a reinhabitable tissue for its anastomosis to the natural urethra.

A preferred embodiment of the bladder according to the invention is provided with two ureteral tubes, each of which opens into it via a urine non-return valve which is seated in the bladder and is preferably of the duckbill type.

In a preferred embodiment of the bladder of the invention, the urine non-return valve of the ureteral tube which is seated in the bladder and is preferably of the duckbill type forms an integral part of the corresponding ureteral tube, with which it is produced in one piece.

Preferably, the bladder of the invention is provided with at least one band of reinhabitable tissue which is attached to the periphery of the upper inner legs of the two W's and can be attached to the peritoneum and is provided with at least one band of reinhabitable tissue attached to the front of the periphery of the upper outer legs of the two W's and with at least one band of reinhabitable tissue attached to the front of the upper wall of the bladder, which bands can be attached by traversing the muscular mass beyond the peritoneum.

According to yet another preferred embodiment of bladder according to the present invention, the bladder is provided, for its suspension, with at least two bands of reinhabitable tissue and, on its vesical neck, with a fixing collar of reinhabitable tissue.

Advantageously the bladder of the invention is made of silicone elastomer and it preferably has a perfectly finished surface state, obtained by the process to which the present invention relates, on its inner-face and on the useful surfaces of its three attached tubes.

The process of the invention insofar as it utilizes a preformed support of non-eliminable material is especially applicable to the manufacture of complete ureters provided with a urine non-return valve, such as those described hereinbefore, by using as a preformed support a solid rod, one end of which is profiled to enable a valve preferably having a duckbill shape to be obtained after moulding, over which rod there is applied by any suitable means a sol of gelose or gelatin which forms by cooling a gel on which a hardenable flexible material such as a silicone elastomer, for example, is deposited, and then, after hardening of the said material, the gel is eliminated by reheating, washing and dissolution and the rod is withdrawn by a simple sliding action to obtain a complete ureter consisting of the said flexible material, in which the inner faces of the valve present the same perfect surface state as the inner face of the tube constituting the ureter.

According to the invention, the above process is also applied to the manufacture of straight or shaped artificial urethras associated if necessary with a sphincter and provided with fixing collars of reinhabitable tissue, such as the urethras described hereinbefore, in association with the bladder according to the invention.

The process of the invention may also be applied to the manufacture of artificial urethras equipped with a sphincter by first of all producing separately, on the one hand, an artificial urethra by the form of the process using a non-eliminable preformed support and, on the other hand, a sphincter constituted by a small balloon, such as that to which French Patent No. 73 40939 relates, by the form of the process using an eliminable support core, and then assembling the two mouldings by introducing the balloon into the opening of the urethral tube and cementing the surfaces which are out of contact with the urine.

Artificial bladders may be produced according to the present invention by employing the form of the process which uses an eliminable support core and can be completed, by cementing, by addition of a sphincter system and two ureters obtained according to the present invention, and in particular the sphincter system to which French Patent No. 73 40939 relates and the ureters provided with fixing collars of reinhabitable tissue and the fixing bands as described above.

The form of the process using a non-eliminable support may be applied with advantage to the production of simple vascular prostheses and in particular to the production, beginning with preformed supports, of vessels or segments of vessels without branches of different or variable calibres over their length.

The form of the process using a completely eliminable support core may be applied with advantage, using support cores moulded in the shape of the desired prosthesis, to the production of complex vascular prostheses with collateral branches or bifurcations.

The form of the process of the invention using a non-eliminable support may be applied with advantage to the production of valvular prostheses and in particular to the moulding of a valvular element according to French Patent No. 74 12107, to which its various appendages are added after moulding.

The process of the present invention may be applied with advantage to the moulding of cardiac prostheses presenting a perfect inner surface state and more particularly to the moulding of ventricular and/or auricular cavities.

Likewise the process of the invention and in particular the form thereof using a support of non-eliminable material, may be applied to the production of the prostheses of very small calibre mentioned hereinbefore and designed to be used in microsurgery in particular in neurological microsurgery, for example, for replacing brain vessels; in cardiac microsurgery, for example, for replacing coronary vessels, and in digestive microsurgery, for example, for replacing the choledoch canal, the splenic, mesenteric, etc. vessels, microvessels and microcanals, which it has been impossible to obtain heretofore with a perfect internal surface state.

In addition to the foregoing features, the invention comprises still more optional features which will appear from the following description.

The invention relates more particularly to processes for the manufacture of organ prostheses in accordance with the foregoing provisions, and to prostheses obtained by carrying these processes into effect and the means for carrying these processes into effect.

BRIEF DESCRIPTION OF DRAWINGS

The invention will be better understood with the aid of the following additional description, which relates to the accompanying drawings, in which:

FIG. 1 is a perspective view showing the general shape of a bladder according to the present invention;

FIG. 2 is cross-sectional view of a bladder according to the present invention in the empty state or in the absence of internal pressure;

FIG. 3 is a cross-section of the bladder according to FIG. 2 in the full state;

FIG. 4 shows diagrammatically a bladder and its appendages according to the present invention, with part of the bladder broken away on the left;

FIG. 5 is a sectional view showing diagrammatically the implantation of a bladder according to the present invention in relation to the peritoneum;

FIG. 8 is a diagrammatic view of a simple vascular prosthesis;

FIG. 9 shows an aortic arch including the initial portions of the two carotid arteries, and FIG. 10 shows a vascular bifurcation.

It should be clearly understood, however, that these drawings and the corresponding parts of the description are given solely by way of illustration of the subject-matter of the invention, of which they do not in any way constitute a limitation.

Referring to the drawings, FIG. 1 is a perspective view showing the ovoid general shape of a bladder according to the present invention. At one end of the ovoid, the bladder 1 is extended by a urethral tube 2. FIG. 1 shows two pairs of bends 3 and 4, 5 and 6, each extending on one side of the bladder 1. These bends 3 to 6 can be seen again in FIG. 2, which is a cross-section of a bladder according to the invention in the empty state or in the absence of internal pressure. Two opposite bends 3 and 5 and 4 and 6 are united by a substantially plane wall 7, 8, respectively. Two bends of a pair, 3 and 4 and 5 and 6, are united by two folds 11 and 12 and 13 and 14, respectively, which are themselves united by a counter-bend 15, 16, respectively. Thus, this cross-section has the form of two W's lying in opposite directions and joined together symmetrically by their outer legs, which are the walls 7 and 8. The inner apices of the W's, which are in counter-bends 15 and 16, substantially touch and the four legs of each W are in contact substantially everywhere in twos: wall and fold 7 and 12, 8 and 11, 8 and 13, 14 and 7. Thus, the residual volume of the bladder 1, that is to say its internal volume in the empty state or in the absence of internal pressure, is practically nil, which constitutes an essential advantage of this construction.

Figure 8:
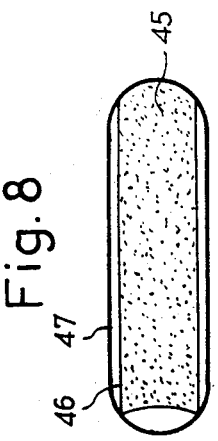
FIGS. 8 to 10 are views of vascular prostheses according to the invention, and in particular.

The shape of the bladder in the empty state is preferably the shape that the free and empty bladder takes, that is to say the shape at rest which is given to it during manufacture. This is not restrictive, however, and it may be sufficient for the bladder to take the said shape when it is emptied under the action of an external pressure, such as, for example, an abdominal pressure on urination.

Likewise, the rounded shapes shown in FIG. 2 for the bends 3, 4, 5 and 6 and the counter-bends 15 and 16 are in no way limitative and other shapes may be obtained in manufacture even angular or square shapes.

FIG. 3, corresponding to FIG. 2, shows the bladder 1 in the full state: the walls 7 and 8 have bulged in a generally elliptical shape, effacing the bends 3, 4, 5 and 6 and unfolding the folds 11, 12, 13 and 14, while the counter-bends are deformed into two more or less depressed parts at the two apices of the long axis of the ellipse. This is not limitative either and still more rounded or less rounded shapes can be allowed.

FIG. 4 shows diagrammatically a bladder and its appendages according to the present invention. The urethral tube 2 can be provided with an artificial sphincter 21, of a type known per se, and with a reinhabitable tissue 22 for anastomosis and attachment to the natural urethra. Two ureteral tubes 23, preferably of silicone elastomer, which are each provided with a urine non-return or check valve 24, open into the bladder 1 laterally and a little to the rear of the vesical neck. These valves 24 are seated in the interior of the bladder 1, as is clearly visible in the broken away part of FIG. 4 (on the left). The valves 24 may be of the duckbill type, which has two flexible lips which open easily and part under even slight pressure in the tube 23 and which close and cling together in the opposite case. Thus, the filling of the bladder takes place easily, which avoids any effect secondary to an over-pressure at the renal level. Each ureteral tube 23 is provided with a fixing collar 25 of reinhabitable tissue and with a sealing collar 26 of reinhabitable tissue for anastomosis to the natural ureter, and possibly with urine drainage holes 27. The bladder 1 is moreover provided, for suspension thereof, with two bands 28 of synthetic tissue (only one of which is visible in FIG. 4) and with a fixing collar 29 of reinhabitable synthetic tissue on its vesical neck. Thus, the bladder according to the invention is positioned leaving free play for the vesical dome in the course of the functional repletions and voidings.

FIG. 5 is a sectional view showing diagrammatically the implantation of a bladder according to the invention in relation to the peritoneum P (for clarity in the drawing, the bladder 1 is shown therein partially filled). This bladder is provided with a band 31 of reinhabitable tissue over the entire periphery of the upper inner legs of the two W's, that is to say over the entire periphery of the folds 11 and 13 close to the upper bends 3 and 5, the band being attached to the peritoneum P, and with two bands 32 and 33 of reinhabitable tissue over the front third of the periphery of the upper outer legs of the two W's, that is to say over the front third of the upper wall 8 close to the upper bends 3 and 5, these bands, like the band 28 already described, being attached by traversing the muscular mass M beyond the peritoneum. It will be noted that the attachment of the band 31 to the peritoneum re-establishes fluid-tightness of the peritoneum, as is essential. It will be observed that, on the one hand, this implantation ensures the necessary fixed points (28, 31, 32, 33) but, on the other hand, allows free extension of the bladder, both during functional repletion (movement of the wall 7 in the direction of the arrow F1 and spreading of the counterbends 15 and 16) and during functional voiding (opposite movements, arrow F2).

The bladder, possibly with its three appended tubes, is of flexible material, preferably silicone elastomer, and it is produced in accordance with the process of the invention by moulding of the flexible material in the liquid state around an eliminable support core of suitable shape and itself having a perfect surface state, which core is eliminated (after the hardening of the flexible material) without degrading the surface state of the flexible material.

Figure 6:
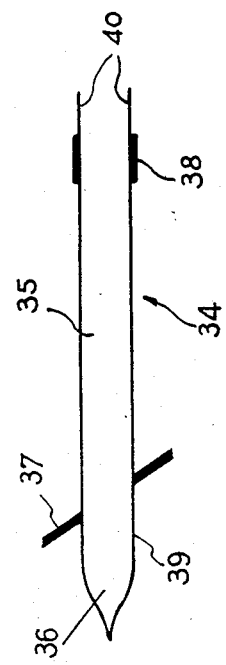
FIG. 6 is a sectional view of the application of the process to which the present invention relates to the production in one piece of a ureter associated with a non-return valve.

The ureter and non-return valve assembly shown in FIG. 6 by way of non-limitative example of the carrying into effect of the process of the invention, and designated in a general manner by the reference 34 is obtained by using as a preformed support a solid metal rod (not shown), one end of which is profiled in the form of a duckbill and which is covered with a gelose sol which gives, by cooling, a gel on which a silicone elastomer is deposited by dipping. After hardening of the latter, the gel "mould" is eliminated by reheating, washing and dissolution in hot water, the rod is withdrawn from the tube 34 by a simple sliding action, and a complete ureter is obtained which comprises a tubular part 35 terminating in a non-return valve 36 which has the shape of a duckbill. The prosthesis obtained in this way is equipped with a collar 37 of reinhabitable tissue for attachment to the bladder and with a sealing ring 38, likewise of reinhabitable tissue, for anastomosis with the natural ureter.

On the placing in position of the prosthesis 34, its part 39 is introduced into the bladder and its part 40 is connected to the residual fraction of the natural ureter.

Figure 7:
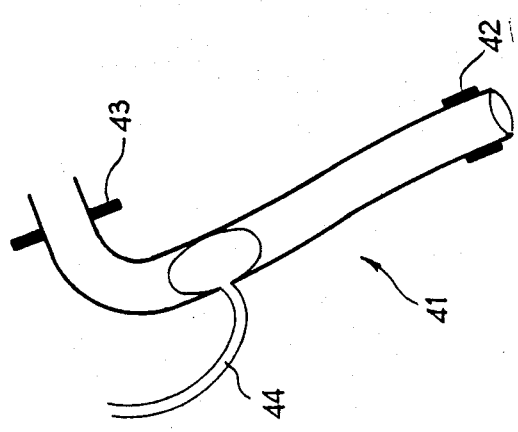
FIG. 7 is a side view of the application of the process to which the present invention relates to the production of a shaped urethra.

FIG. 7 shows, likewise by way of non-limitative example of the carrying into effect of the process of the invention a "shaped" urethra which has the function of permitting diversion of the urine in the bladder either towards the distal section of the natural urethra, or directly to the skin. Such a urethra, designated in a general manner by the reference 41, is obtained by using a rod of rigid material preformed to the desired shape which is coated with gelose gel and then with silicone elastomer, the gel being eliminated by hot washing and dissolution when the elastomer has hardened on the mould and the rod being then withdrawn by a simple sliding action. The urethra 41 obtained in this way is then equipped with fixing ring 42 of reinhabitable tissue, an artificial sphincter 44 and a collar 43, likewise of reinhabitable tissue, for attachment to the bladder.

FIG. 8 illustrates the process of manufacture of a simple vascular prosthesis. A non-eliminable preformed mould 45 is covered, according to the invention, with a gelose sol which, by cooling, forms a gel 46 which is then subjected to the action of heat by projecting steam in order to give it a surface state close to that of the liquid-air interface. Once this surface state has been obtained, a hardenable flexible material, such as a silicone elastomer, is deposited on the gel coating 46 by dipping. By hardening of the silicone elastomer, a coating 47 is obtained and the gel coating 46 is eliminated by reheating, washing and dissolution and the mould is then withdrawn from the moulded prosthesis.

The deposit of the silicone elastomer 47 on the gel coating 46 may be effected by successive dippings to give the required thickness to the coating of silicone elastomer.

In this way, a simple vascular prosthesis is obtained, that is to say without any branches.

Figure 9:
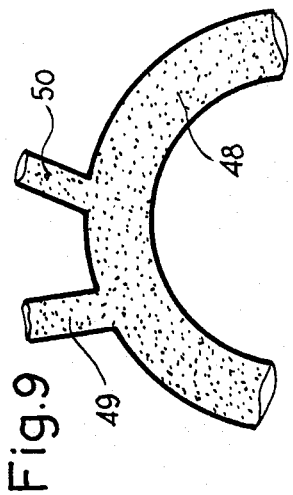

FIG. 9 shows an aortic arch 48 comprising the initial portions 49 and 50 of the carotid arteries.

A complex vascular prosthesis of this kind is produced from silicon elastomer with the aid of an eliminable preformed mould, such as a wax mould, for example, which is eliminated by melting and then dissolution with a hot liquid, after hardening of the silicone elastomer coating.

Figure 10:
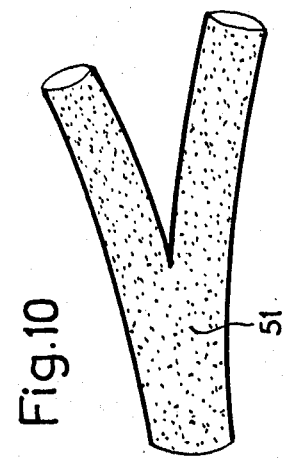

FIG. 10 shows another complex vascular prosthesis according to the invention comprising a bifurcation. This vascular prosthesis is constituted by a vascular bifurcation 51 likewise produced from silicone elastomer by moulding on an eliminable support core after hardening of the silicone elastomer.

According to an advantageous embodiment of the subject-matter of the invention, some of the organ prostheses produced according to the present invention may be used in an external position; for example, in the case of a prosthetic bladder produced according to the invention, this may be attached to a patient by a belt of suitable form, the two ureters of the said prosthetic bladder which are produced according to the present invention connecting the two natural ureters inosculated at the skin.

Likewise, according to the present invention, a prosthetic urethra according to the invention may be associated with advantage with a surgically formed reservoir known by the name "Bricker", to which it is fixed externally.

It is apparent from the foregoing description that, whatever the methods of carrying into effect, embodiments and modes of application adopted, processes of manufacture of organ prostheses and prostheses produced with the aid of these processes are obtained which present important advantages with respect to the processes and prostheses known heretofore, some of which advantages have been mentioned in the foregoing and others of which will become apparent in the course of the use of the said processes and prostheses.

As is apparent from the foregoing, the invention is by no means limited to those methods of carrying it into effect, embodiments and modes of application thereof which have just been more explicitly described; on the contrary, it covers all modifications which may come to the minds of those skilled in the art, without departing from the framework or the scope of the present invention.

We claim:

1. An organ prosthesis, having an internal surface adapted to be in contact with body fluids, formed of a flexible material having an internal surface state devoid of roughness, whereby formation of concretions and deposits, fibrinous coagulum and calculi or lithiasis, during use of the organ prosthesis, due to the roughness, is avoided, and obtained by molding, said organ prosthesis being formed by forming, on a preformed support in the shape of the prosthesis, a coating of a sol selected from the group consisting of gelose and gelatin giving, on cooling, a gel having a surface state approximately the same as the liquid-air interface of gelose or gelatin in solution at its surface not adjacent the support, said coating being formed by dipping, spraying, coating, varnishing or lacquering the sol on the support, forming said gel from said sol, then forming a hardenable flexible material coating of silicon elastomer compatible with the body liquids and tissues on the gel, the flexible material coating being formed by dipping, flowing or spraying, the flexible material coating taking the shape of the preformed support in the shape of the prosthesis, then hardening the hardenable flexible material, the hardened flexible material having a surface state adjacent said gel that is devoid of roughness, and separating the hardened flexible material and the preformed support, the hardened flexible material being the organ prosthesis, wherein the preformed support is in the shape of a ureter prosthesis, a urethra prosthesis, a vascular prosthesis, a valvular prosthesis, a cardiac prosthesis, or a bladder prosthesis, whereby the organ prosthesis of the hardened flexible material is, respectively, a ureter prosethesis, a urethra prosthesis, a vascular prosthesis, a valvular prosthesis, a cardiac prosthesis or a bladder prosthesis.

2. An organ prosthesis according to claim 1, wherein the preformed support is made of a non-eliminable material which has a surface without any rough or uneven areas, and wherein the hardened flexible material is separated from the preformed support by heating the coated support and washing out said gel coating, and then sliding the hardened flexible material, whose internal dimensions are larger than the external dimensions of the preformed support due to elimination of the gel coating, off the preformed support.

3. An organ prosthesis according to claim 1, wherein the preformed support is obtained by molding a core of completely eliminable material in a removable mold whose molding surfaces are devoid of any unevenness, thereby forming a preformed support in the shape of the prosthesis after removal of the mold, said preformed support having a surface without any unevenness, and wherein the hardened flexible material and the preformed support are separated by melting the support and washing the support away with a hot liquid.

4. An organ prosthesis according to claim 2, wherein the prosthesis is a complete ureter prosthesis provided with a non-return valve of duckbill type forming an integral part of the ureter.

5. Ureter prosthesis according to claim 4, characterised in that, in order to ensure its fluid-tightness, each ureteral tube is provided with a fixing collar of reinhabitable tissue close to its non-return valve, and with a sealing collar of reinhabitable tissue for its anastomosis with the natural ureter.

6. An organ prosthesis according to claim 2, wherein the prosthesis is a straight artificial urethra.

7. An organ prosthesis according to claim 2, wherein the prosthesis is a shaped artificial urethra.

8. Urethra according to claim 6, associated by insertion and cementing with a sphincter.

9. Urethra according to claim 7, associated by insertion and cementing with a sphincter.

10. An organ prosthesis according to claim 2, wherein the prosthesis is a vascular prosthesis without any branches.

11. An organ prosthesis according to claim 2, wherein the prosthesis is a complex vascular prosthesis with branches and/or bifurcations.

12. An organ prosthesis according to claim 3, wherein the prosthesis is a complex vascular prosthesis with branches and/or bifurcations.

13. An organ prosthesis according to claim 1, wherein the prosthesis is a valvular prosthesis.

14. An organ prosthesis according to claim 2, wherein the prosthesis is a valvular prosthesis.

15. An organ prosthesis according to claim 1, wherein the prosthesis is a cardiac prosthesis.

16. An organ prosthesis is according to claim 2, wherein the prosthesis is a cardiac prosthesis.

17. An organ prosthesis according to claim 3, wherein the prosthesis is a cardiac prosthesis.

18. An organ prosthesis according to claim 1, said prosthesis being a vascular prosthesis of very small calibre designed to be used in microsurgery.

19. An organ prosthesis according to claim 2, said prosthesis being a vascular prosthesis of very small calibre designed to be used in microsurgery.

20. An organ prosthesis according to claim 3, wherein the prosthesis is an artificial bladder of flexible material and ovoid general shape characterised in that, in the empty state or in the absence of internal pressure, it has transversely the form of two W's lying in opposite directions and joined together symmetrically by their outer legs and in which the inner apices substantially touch and the four legs of each W are in contact substantially everywhere in twos, in that its surfaces in contact with urine are in a surface state devoid of roughness, and in that it is provided with means of suspension at least three points.

21. Artificial bladder according to claim 20, characterised in that its ovoid general shape is extended at one end by a urethral tube by association with an artificial urethra which urethral tube is provided with a reinhabitable tissue for its anastomosis to the natural urethra.

22. Artificial bladder according to claim 20, characterised in that it is provided with two ureteral tubes each of which debouch through a urine non-return valve, which valve is seated in the bladder and is of the duckbill type.

23. Artificial bladder according to claim 20, characterised in that for the purpose of its implantation it is provided with at least one band of reinhabitable tissue which is attached to the periphery of the upper inner legs of the two W's and is adapted to be attached to the peritoneum, and in that it is provided with at least one band of reinhabitable tissue attached to the front third of the periphery of the upper outer legs of the two W's and with at least one band of reinhabitable tissue attached to the front of the upper wall of the bladder which bands are adapted to be attached by traversing the muscular mass beyond the peritoneum.

24. Artificial bladder according to claim 23, characterised in that its ovoid general shape is extended at one end by a urethral tube by association with an artificial urethra which is provided with a reinhabitable tissue for its anastomosis to the natural urethra.

25. Artificial bladder according to claim 23, characterised in that it is provided with two artificial ureteral tubes each of which debouch through a urine non-return valve, which valve is seated in the bladder and is of the duckbill type.

26. Artificial bladder according to claim 20, characterised in that for the purpose of its implantation it is provided, for its suspension, with at least two bands of reinhabitable tissue and, on its vesical neck, with a fixing collar of reinhabitable tissue.

27. Artificial bladder according to claim 20, characterised in that for the purpose of its use in an external position it comprises a belt enabling it to be attached to a patient, with two artificial ureters associated with the said prosthetic bladder and adapted to be connected to the two natural ureters inosculated at the skin.

28. A prosthetic urethra according to claim 6, characterised in that the said prosthetic urethra is associated with a surgically formed reservoir to which it is fixed externally.

29. An organ prothesis according to claim 2, wherein said non-eliminable material is selected from the group consisting of metal, glass and plastics.

30. An organ prosthesis according to claim 3, wherein said completely eliminable material is selected from the group consisting of wax, ceresin, and a sol giving a gel upon cooling.

31. An organ prosthesis according to claim 3, wherein the removable mold is made of a material selected from the group consisting of metal and plastics.

32. Urethra according to claim 6, wherein said sphincter is formed by molding a core of completely eliminable material in the shape of a sphincter, applying a coating of said sol capable of forming a gel upon hardening to said core, and forming said gel, said gel having a surface state approximately the same as the liquid-air interface at its surface not adjacent the core, coating and then hardening said hardenable flexible material on said gel, and then eliminating said core, whereby the hardened flexible material constitutes said sphincter.

33. Cardiac prosthesis according to claim 16, wherein the prosthesis is an artificial ventricular and/or auricular cavity.

34. Ureter prosthesis according to claim 5, wherein each ureteral tube is further provided with urine drainage holes.

35. Urethra according to claim 7, wherein said sphincter is formed by molding a core of completely eliminable material in the shape of a sphincter, applying a coating of said sol capable of forming a gel upon hardening to said core, and forming said gel, said gel having a surface state approximately the same as the liquid-air interface at its surface not adjacent the core, coating and then hardening said hardenable flexible material on said gel, and then eliminating said core, whereby the hardened flexible material constitutes said sphincter.

36. Cardiac prosthesis according to claim 17, wherein the prosthesis is an artificial ventricular and/or auricular cavity.

37. An organ prosthesis according to claim 18, wherein said vascular prosthesis is designed to be used in neurological microsurgery, cardiac microsurgery, or digestive microsurgery.

38. An organ prosthesis according to claim 19, wherein said vascular prosthesis is designed to be used in neurological microsurgery, cardiac microsurgery, or digestive microsurgery.

39. Artificial bladder according to claim 21, wherein said artificial urethra is formed by applying a coating of said sol capable of forming a gel upon hardening to a non-eliminable preformed support in the shape of a urethra, forming said gel from said sol, coating and then hardening said hardenable flexible material on said gel, and then removing the hardened flexible material from the preformed support, whereby the hardened flexible material constitutes said artificial urethra.

40. Artificial bladder according to claim 39, characterised in that it is provided with two ureteral tubes each of which debouch through a urine non-return valve, which valve is seated in the bladder and is of the duckbill type.

41. Artificial bladder according to claim 40, wherein each of said ureteral tubes has said non-return valve formed as an integral part thereof, and wherein each of said ureteral tubes are formed by applying a coating of said sol capable of forming a gel upon hardening to a non-eliminable preformed support in the shape of a ureter, forming said gel from said sol, coating and then hardening said hardenable flexible material on said gel, and then removing the hardened flexible material from the preformed support, whereby the hardened flexible material constitutes said ureteral tube.

42. Artificial bladder according to claim 22, wherein each of said ureteral tubes has said non-return valve formed as an integral part thereof, and wherein each of said ureteral tubes are formed by applying a coating of said sol capable of forming a gel upon hardening to a non-eliminable preformed support in the shape of a ureter, forming said gel from said sol, coating and then hardening said hardenable flexible material on said gel, and then removing the hardenable flexible material from the preformed support, whereby the hardened flexible material constitutes said ureteral tube.

43. An organ prosthesis, having an internal surface adapted to be in contact with body fluids, formed of a flexible material having an internal surface state devoid of roughness, whereby formation of concretions and deposits, fibrinous coagulum and calculi or lithiasis, during use of the organ prosthesis, due to the roughness, is avoided, and obtained by molding, said organ prosthesis being formed by forming, on a preformed support in the shape of the prosthesis, a coating of a sol selected from the group consisting of gelose and gelatin giving, on cooling, a gel having a surface state approximately the same as the liquid-air interface of gelose or gelatin in solution at its surface not adjacent the support, wherein the preformed support is made of a non-eliminable material which has a surface without any rough or uneven areas, said coating being formed by dipping, spraying, coating, varnishing or lacquering the sol on the support, forming said gel from said sol, then forming a hardenable flexible material coating of silicone elastomer compatible with the body liquids and tissues on the gel, the flexible material coating being formed by dipping, flowing or spraying, the flexible material coating taking the shape of the preformed support in the shape of the prosthesis, then hardening the hardenable flexible material, the hardened flexible material having a surface state adjacent said gel that is devoid of roughness, and separating the hardened flexible material and the preformed support, wherein the hardened flexible material is separated from the preformed support by heating the coated support and washing out said gel coating, and then sliding the hardened flexible material, whose internal dimensions are larger than the external dimensions of the preformed support due to elimination of the gel coating, off the preformed support, the hardened flexible material being the organ prosthesis.

44. An organ prosthesis, having an internal surface adapted to be in contact with body fluids, formed of a flexible material having an internal surface state devoid of roughness, whereby formation of concretions and deposits, fibrinous coagulum and calculi or lithiasis, during use of the organ prosthesis, due to the roughness is avoided, and obtained by molding, said organ prosthesis being formed by forming, on a preformed support in the shape of the prosthesis, a coating of a sol selected from the group consisting of gelose and gelatin giving, on cooling, a gel having a surface state approximately the same as the liquid-air interface of gelose or gelatin in solution at its surface not adjacent said support, wherein the preformed support is obtained by molding a core of completely eliminable material in a removable mold whose molding surfaces are devoid of any unevenness, thereby forming a preformed support in the shape of the prosthesis after removal of the mold, said preformed support having a surface without any unevenness, said coating being formed by dipping, spraying, coating, varnishing, or lacquering the sol on the support, forming said gel from said sol, and forming a hardenable flexible material coating of silicone elastomer compatible with the body liquids and tissues on the gel, the flexible material coating being formed by dipping, flowing or spraying, the flexible material coating taking the shape of the preformed support in the shape of the prosthesis, then hardening the hardenable flexible material, the hardened flexible material having a surface state adjacent said gel that is devoid of roughness, and separating the hardened flexible material and the preformed support, the hardened flexible material and preformed support being separated by melting the support and washing the support away with a hot liquid, the hardened flexible material being the organ prosthesis.

* * * * *